United States Patent [19]

Nakamura et al.

[11] Patent Number: 4,786,630

[45] Date of Patent: Nov. 22, 1988

[54] SOLVENT OF A CHROMOGENIC DYE-PRECURSOR MATERIAL FOR PRESSURE-SENSITIVE RECORDING PAPER, THE PRESSURE-SENSITIVE RECORDING PAPER AND PROCESS FOR PRODUCING THE SOLVENT

[75] Inventors: Tadashi Nakamura; Takashi Terauchi; Shoichi Hoshi, all of Iwaki, Japan

[73] Assignee: Kureha Kagaku Kogyo Kabushiki Kaishi, Tokyo, Japan

[21] Appl. No.: 136,722

[22] Filed: Dec. 22, 1987

Related U.S. Application Data

[62] Division of Ser. No. 872,091, Jun. 6, 1986, Pat. No. 4,737,189.

[30] Foreign Application Priority Data

Jun. 13, 1985 [JP] Japan .............................. 60-128573
Jun. 13, 1985 [JP] Japan .............................. 60-128574

[51] Int. Cl.$^4$ ...................... B41M 5/16; B41M /5/18
[52] U.S. Cl. .................................. 503/213; 427/150; 427/151; 428/195; 428/914; 503/215
[58] Field of Search ................. 106/21; 427/150–152; 428/195, 914; 503/213, 215

[56] References Cited

U.S. PATENT DOCUMENTS

| | | | |
|---|---|---|---|
| 4,130,299 | 12/1978 | Wygant | 427/150 |
| 4,529,681 | 7/1985 | Usami et al. | 430/151 |
| 4,559,242 | 12/1985 | Mitsuo et al. | 427/150 |
| 4,598,035 | 9/1986 | Usami et al. | 430/171 |

FOREIGN PATENT DOCUMENTS

| | | | |
|---|---|---|---|
| 0075494 | 3/1983 | European Pat. Off. | 427/150 |
| 2079804 | 1/1982 | United Kingdom | 427/150 |

OTHER PUBLICATIONS

Watanabe; Image Recording Material, (Fuji Photo Film Co, Ltd.); 93: 58285.

*Primary Examiner*—Bruce H. Hess
*Attorney, Agent, or Firm*—David G. Conlin; Ronald I. Eisenstein

[57] ABSTRACT

Disclosed herein are (1) a solvent of a chromogenic dye-precursor material for pressure-sensitive recording paper, which solvent comprises a diarylalkanes containing not less than 80% by weight of a mixture of 1-tolyl-2-phenylpropane and 1,2-ditolylethane, obtained by coupling ethylbenzene and xylene by side-chain dehydrogenation, (2) the pressure-sensitive recording paper sheet prepared by using the solvent and (3) a process for producing the solvent.

2 Claims, No Drawings

SOLVENT OF A CHROMOGENIC DYE-PRECURSOR MATERIAL FOR PRESSURE-SENSITIVE RECORDING PAPER, THE PRESSURE-SENSITIVE RECORDING PAPER AND PROCESS FOR PRODUCING THE SOLVENT

This is a divisional of co-pending application Ser. No. 872,091 filed on 6/6/86 now U.S. Pat. No. 4,737,189.

BACKGROUND OF THE INVENTION

The present invention relates to a solvent of a chromogenic dye-precursor material for preparing a pressure-sensitive recording paper sheet excellent in the stability in preservation of the colour-developed images and in the colour-developer under severe coldness, a pressure-sensitive recording paper sheet prapared by using the solvent and a process for producing the solvent comprising coupling ethylbenzene and xylene by side-chain dehydrogenation. More in detail, the present invention relates to (1) a solvent of a chromogenic dye-precursor material for preparing a pressure-sensitive recording paper sheet, which the solvent comprises diarylalkanes containing not less than 80% by weight of a mixture of 1-tolyl-2-phenylpropane and 1,2-ditolylethane, obtained by coupling ethylbenzene and xylene by side-chain dehydrogenation, (2) a pressure-sensitive recording paper sheet prepared by using the solvent comprising diarylalkanes of a chromogenic dye-precursor material (colour former), and (3) a process for producing the solvent of a chromogenic dye-precursor material for a pressure-sensitive recording paper sheet, which process comprises coupling ethylbenzene and xylene by side-chain dehydrogenation at a temperature of not less than 100° C. in the presence of a peroxodisulfate.

The mixture of dimers obtained by the liquid-phase coupling method of ethylbenzene and xylene contains 1,2-ditolylethane, 1-tolyl-2-phenylpropane and 2,3-diphenylbutane, and since these dimers are aromatic compounds boiling at higher temperatures, the thus obtained mixture of dimers is useful as an organic thermal medium and an electric insulating oil other than the solvent of the chromogenic dye-precursor material for the pressure-sensitive recording paper sheet.

In general, the pressure-sensitive recording paper sheet is composed of (1) a combination of a paper sheet (hereinafter referred to as "CB paper") on the back side of which microcapsules containing a solution of a colourless electron-donator having a colouring reactivity (hereinafter referred to as "chromogenic dye-precursor material") has been applied and another paper sheet (hereinafter referred to as "CF paper") on the upper side of which a colour-developing agent (hereinafter referred to as "colour-developer") having an ability of forming a coloured product by reacting with the above-mentioned chromogenic dye-precursor material has been applied, (2) a paper sheet (hereinafter referred to as "CFB paper") on one side of which the microcapsules have been coated therewith and on the other side of which the colour-developer has been coated therewith, (3) a combination of the CB paper and CF paper or (4) a paper sheet on one side of which the microcapsules and the colour-developer are coated therewith in the form of layer or a mixture of the microcapsules and the colour-developer are coated therewith. On applying an artificial pressure on every one of the pressure-sensitive recording paper sheet, the microcapsules on the thus pressured part are broken to make the chromogenic dye-precursor material and the colour-developer in contact each other, thereby developing a colour.

In the pressure-sensitive recording paper sheet, the materials which exert an important influence on the quality thereof are the solvent of the chromogenic dye-precursor material contained in the microcapsule and the wall material forming the microcapsule.

Hitherto, the specificities required to the solvent of the chromogenic dye-precursor material for the pressure-sensitive recording paper sheet have been the followings.

(1) The solubility of the chromogenic dye-precursor material in the solvent is high.

(2) The colour-developing rate is high, the concentration of the thus developed colour is high and the stability of the colour tone is also high after the colour-development.

(3) The solvent is stable against lights, heat and chemicals.

(4) The solvent is substantially odorless.

(5) The solvent is harmless to human body and free from danger.

(6) The solvent is favorably biodegradable not to cause environmental pollution.

However, with the propagation of the use of the pressure-sensitive recording paper sheet together with the rapid development of electronics, the qualitative requirements to the developed colour image have come to be severer.

Namely, the pressure-sensitive recording paper sheet have come to be used for recording in the outdoor services such as gas stations in cold districts, and the colour-developed pressure-sensitive recording paper sheet have come to be preserved for a long time as the recorded documents.

According to the change of the situations around the pressure-recording paper sheet, the following requirements to the performances of the pressure-sensitive recording paper sheet have been issued.

(1) The stability in preservation of the colour-developed image obtained by pressure-sensitive recording is improved.

(2) The recorded documents prepared by using the pressure-sensitive recording paper sheet are substantially odorless in placing it in storage.

(3) The pressure-sensitive recording paper sheet exhibit excellent colour-developing property.

It has been considered that it is extremely difficult to provide the pressure-sensitive recording paper sheet which satisfies the above-mentioned new requirements.

Ordinarily, the pressure-sensitive recording paper sheet is kept at room temperature for about 6 months before colour-development and for one to two years after colour-development, and the stability in preservation of the sheets for such a long time depends fundamentally on the chromogenic dye-precursor material, the colour-developer and the solvent of the chromogenic dye-precursor material. Particularly, concerning the solvent of the chromogenic dye-precursor material, a low-boiling solvent which evaporates just after performing its role as the carrier of the chromogenic dye-precursor material and as the medium of colour-developing reaction has been regarded as desirable.

However, since the pressure-sensitive recording paper sheet prepared by using such a solvent is not only poor in stability in preservation but also smell badly, such a solvent could not be said to be the solvent of chromogenic dye-precursor material for the pressure-sensitive recording paper sheet, which satisfies the above-mentioned requirements.

For instance, as the solvent of chromogenic dye-precursor material for the pressure-sensitive recording paper sheet, which has been hitherto used, the following compounds may be proposed.

Diisopropylnaphthalenes, 1-xylyl-1-phenylethanes, xylylphenylmethanes, partially hydrogenated terphenyls and butylbiphenyls.

Of the above-mentioned solvents of chromogenic dye-precursor material, partially hydrogenated terphenyl is excellent stability in preservation of the colour-developed image, however, the colour-developing activity of the solvent at a temperature of not higher than $-5°$ C. is extremely poor. In addition, although 1-xylyl-1-phenylethanes are excellent in colour-developing activity at low temperatures, it has a demerit of extremely strong in odor.

Other than the above-mentioned solvents, the following compounds have been proposed as the solvent of chromogenic dye-precursor material for the pressure-sensitive recording paper sheet. 1,2-Ditolylethanes (refer to U.S. Pat. No. 3,836,383), 1,1-Ditolylethanes (refer to U.S. Pat. No. 3,836,383) and 1,2-Ditolylpropanes (refer to Japanese Patent Application Laying-Open (KOKAI) No. 48-15611 (1973)).

As the synthetic method of 1,2-ditolylethanes disclosed in U.S. Pat. No. 3,836,383, the method following the Fiedel-Crafts reaction between toluene and 1,2-dichloroethane is adopted in general.

Since the synthesized product contains about 30% by weight of easily crystallizable 4,4'-dimethyl-1,2-diphenyl ethane which 4,4'-dimethyl-1,2-diphenylethane crystallizes out from the product at a low temperature of $-5°$ to $0°$ C., the synthesized product is not preferable as the solvent of chromogenic dye-precursor material.

The trouble due to the precipitation of crystals occurs at the time of microcapsulation, of recording the pressure-sensitive recording paper sheet and of handling the solvent of chromogenic dye-precursor material.

For instance, on using the pressure-sensitive recording paper sheet at a low temperature of not higher than $-5°$ C., since a part of the solvent of chromogenic dye-precursor material crystallizes out from the solvent, the amount of the chromogenic dye-precursor material which dissolves in the solvent is reduced. As a result of the reduction, crystals of the chromogenic dye-precursor material are precipitated from the solvent. On carrying out the pressure-sensitive recording in such a situation, the recording is incompletely carried out because of the insufficient reaction between the chromogenic dye-precursor material and the colour-developer.

In addition, 1,1-ditolylethanes obtained by condensation of toluene with acetoaldehyde or by the reaction between toluene and 1,1-dichloroethane is poor in the stability in preservation of the colour-developed image.

Further, also 1,2-ditolylpropane obtained by the reaction between toluene and 1,2-dichloropropane or 1,2-ditolylpropanes obtained by the reaction between toluene and allyl chloride is poor in the stability in preservation of the colour-developed image.

Namely, with the remarkable propagation of the pressure-sensitive recording paper sheet and the change of the environment, an offer of a solvent of chromogenic dye-precursor material which is excellent in the stability in preservation of the colour-developed image and in the colour-developing activity at a low temperature of not higher than $-5°$ C. and is almost odorless, namely, a solvent to be put to practical use, has been keenly demanded.

On the other hand, concerning the coupling reaction by side-chain dehydrogenation, several methods have hitherto been known, for instance, a method of oxidative coupling of toluene at a temperature of 400° to 600° C. in the presence of a metal oxide catalyst has been known.

In Japanese Patent Application Laying-Open (KOKAI) No. 58-159428 (1983), a method of producing a dimer of toluene has been disclosed, wherein toluene is reacted in the presence of a certain quaternary ammonium salt in an aqueous solution of a peroxodisulfate. According to the above-mentioned method, although the dimer is obtained in a high yield, since it is necessary to use a large amount of the expensive quaternary ammonium salt, the method cannot be said to be an industrially desirable method.

The Japanese Patent Application Laying-Open (KOKAI) No. 58-159428 (1983) further discloses a process wherein the peroxodisulfate is regenerated by an electrochemical method.

However, in the case of electrochemically regenerating the peroxodisulfate, although the current efficiency is higher as the concentration of the sulfate ions is higher and it is desirable to maintain the high concentration of the sulfate ions, since the yield of the dimer is reduced by the presence of the sulfate ions at higher concentrations in the case of the coupling, the method cannot be said to be practical method. In addition, in the method, the addition of $Ag^+$ or ions of transition metals to the reaction system for raising the yield of coupling causes a demerit of making the electrochemical regeneration difficult.

Namely, an offer of a method for liquid-phase coupling of ethylbenzene and xylene, by which the dimer can be obtained in a high yield and the peroxodisulfate can be electrochemically regenerated without using the expensive quaternary ammonium salt has been eagerly demanded.

As a result of the present inventors' studies for solving the above-mentioned problems, it has been found that by subjecting a mixture of ethylbenzene and xylene to "coupling by side-chain dehydrogenation" at a temperature of not less than 100° C. in the presence of an aqueous solution of the peroxodisulfate, (1) diaryalkanes comprising 1,2-ditolylethanes, 1-tolyl-2-phenylpropanes and 2,3-diphenylbutane is obtained and (2) the thus obtained diarylalkanes has the excellent specificities as the solvent of chromogenic dye-precursor material for the pressure-sensitive recording paper sheet, is excellent in the stability in preservation of the colour-developed image and in the colour-developing activity at lower temperatures, and is almost odorless. Based on the above-mentioned findings, the present inventors have attained the present invention.

Namely, the objective of the present invention is to provide a solvent of chromogenic dye-precursor material for the pressure-sensitive recording paper sheet, the solvent comprising diarylalkanes which shows an excellent stability in preservation of the colour-developed image and an excellent colour-developing activity at a low temperature of not higher than $-5°$ C. and is almost odorless.

Furthermore, the objective of the present invention is to provide a process for producing diarylalkanes in a high yield by subjecting a mixture of ethylbenzene and xylene to "coupling by side-chain dehydrogenation" at a temperature of not less than 100° C. in the presence of an aqueous solution of a peroxodisulfate.

In addition, another objective of the present invention is to provide a process for "coupling by side-chain dehydragenation", by which the dimer can be produced even in the presence of a high concentration of sulfate ions necessary for obtaining the high current efficiency in the case of electrochemically regenerating the peroxodisulfate from the aqueous solution after performing the reaction of "coupling by side-chain dehydrogenation".

SUMMARY OF THE INVENTION

In a first aspect of the present invention, there is provided a solvent of chromogenic dye-precursor material for a pressure-sensitive recording paper sheet, the solvent comprising diarylalkanes containing not less than 80% by weight of 1-tolyl-2-phenylpropanes and 1,2-ditolylethanes, obtained by subjecting ethylbenzene and xylene to "coupling by side-chain dehydrogenation".

In a second aspect of the present invention, there is prodived a pressure-sensitive recording paper sheet in which diarylalkanes containing more than 80% by weight of 1-tolyl-2-phenylpropanes and 1,2-ditolylethanes is used as the solvent of chromogenic dye-precursor material.

In a third aspect of the present invention, there is provided a process for producing the solvent of chromogenic dye-precursor material for a pressure-sensitive recording paper sheet, comprising reacting a mixture of ethylbenzene and xylene to a temperature of not less than 100° C. in the presence of an aqueous solution of a peroxodisulfate, thereby causing "coupling by side-chain dehydrogenation" of ethylbenzene and xylene.

DETAILED DESCRIPTION OF THE INVENTION

Diarylalkanes according to the present invention is available by subjecting ethylbenzene and xylene to "coupling by side-chain dehydrogenation". As the method of "coupling by side-chain dehydrogenation", there is a method wherein the reaction is carried out in the presence of a basic metal oxide catalyst or a method wherein the reaction is carried out in the presence of a radical-generator such as peroxodisulfate in liquid phase.

According to the method carried out in liquid phase in the presence of the radical-generator, ethylbenzene is reacted to xylene in an aqueous solution of peroxodisulfate, and the reaction is accelerated by the addition of metal ions such as $Fe^{2+}$ and $Ag^+$ or a quaternary ammonium salt.

In addition, even in the case of without using the metal ions or peroxodisulfate, it is able to obtain 1-tolyl-2-phenylethanes and 1,2-ditolylethanes in a high yield when the reaction of "coupling by side-chain dehydrogenation" is carried out at a molar ratio of the raw material (mixture of ethylbenzene and xylene) to peroxodisulfate from 2.5:1 to 4.5:1 at a higher temperature, for instance, a temperature of not less than 100° C., preferably from 120° to 200° C., and most preferably from 150° to 180° C. for from 15 min to 4 hours, preferably from 30 min to 2 hours.

In the case where the reaction temperature is under 100° C., the reaction of "coupling by side-chain dehydrogenation" does not sufficiently proceeds resulting in the low yield of the diarylalkanes and causing the main reaction of oxidation of alkyl side-chain of the aromatic compounds. On the other hand, in the case where the reaction is carried out at a temperature of over 100° C., oxidation of alkyl side-chain scarcely proceeds and the formation of the aromatic compound having an oxygen-containing side-chain group is reduced to the substantially negligible extent.

The reaction of "coupling by side-chain dehydrogenation" of alkylbenzene in the presence of an aqueous solution of peroxodisulfate according to the present invention is shown as follows.

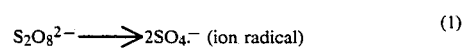

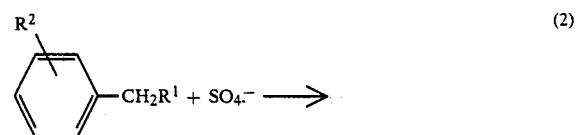

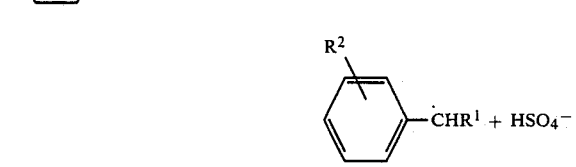

(wherein $R^1$ and $R^2$ represent respectively a hydrogen atom or a methyl group).

The thus formed benzyl radicals form a dimer as shown in the formula (3) or are further oxidized to be benzyl cation as shown in the formula (4) as follows.

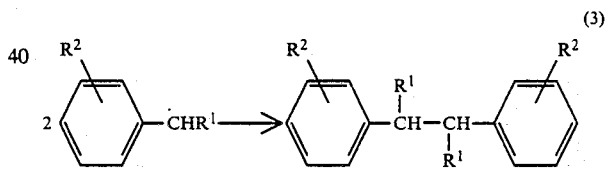

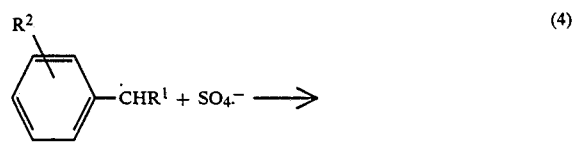

From the thus formed benzyl cation, aromatic compounds having the oxygen-containing group provided with hydroxyl group(s) or carbonyl group(s) are formed.

One of the methods for suppressing the occurrence of the reaction shown by the formula (4) is to make so that the sulfate ion radical ($SO_4^-\cdot$) concerns chiefly to the reaction shown in the formula (2). Such an effect is attained by carrying out the "coupling by side-chain dehydrogenation" at high temperatures, for instance, at a temperature of not less than 100° C. The high temperature is more preferably in the reaction proceeds, however, since the reaction pressure becomes higher than what is necessary at an excessively high temperature, the too much high temperature is not desirable.

In the case where the reaction of "coupling by side-chain dehydrogenation" is carried out in batch mode, the improvement of the rate of conversion and the selectivity rate of coupling are not effected sufficiently only by raising the reaction temperature to, for instance, not less than 100° C. The reason of this fact is due to the consumption of the larger part, or according to circumstances, to the consumption of the whole of peroxodisulfate during the period wherein the aqueous solution of peroxodisulfate and the mixture of ethylbenzene and xylene are heated from room temperature to the predetermined reaction temperature while stirring. Namely, since peroxodisulfate is cleaved into two radicals by heating and the cleaving rate is raised with elevating the reaction temperature, the characteristic reaction of ethylbenzene and xylene at a high temperature is difficultly carried out.

Accordingly in the present invention, after heating a mixture of ethylbenzene and xylene to a predetermined temperature, preferably, while dispersing the mixture of ethylbenzene and xylene in an aqueous medium by stirring thereof, the aqueous solution of peroxodisulfate is added to the thus formed aqueous dispersion. By the above-mentioned procedures, the deactivation rate of peroxodisulfate is reduced, and the formation of the by-products such as an aromatic compound which has hydroxyl group or carbonyl group and the consumption of a large amount of peroxodisulfate from the benzyl cation are also reduced, and as a result, it becomes possible to utilize peroxodisulfate as far as possible, thereby remarkably improving the conversion rate of ethylbenzene and xylene and the coupling selectivity.

In the case of adding the aqueous solution of peroxodisulfate to the aqueous dispersion of ethylbenzene and xylene, the whole of the predetermined amount of the aqueous solution of peroxodisulfate may be added at a time, however, it is preferable to add dropwise. Such a dropping step is preferably carried out for longer than 2 min, more preferably for longer than 5 min in order to obtain a high conversion rate and a high selectivity. However, it is not desirable to reduce the dropping speed to much, because such a procedure takes time longer than the necessity. The optimum time period of dropping depends on the economic property of the process.

By preliminarily heating the mixture of ethylbenzene and xylene to the predetermined reaction temperature, not only the conversion and the selectivity of dimerization are remarkably improved but also the reaction time is profitably reduced, and in the batch mode, the reaction of dimerization completes ordinarily within one hour, and as the case may be, within about 10 min.

The ratio of ethylbenzene to xylene in the coupling according to the present invention may be optionally selected.

For instance, as the raw material according to the present invention, "mixed xylene" commercialized a solvent may be mentioned. For instance, "mixed xylene" is obtained in the case of naphtha-cracking and also obtained in the case of operating the catalytic reforming.

"Mixed xylene" obtained from naphtha-cracking contains about 45% by weight of ethylbenzene, and "mixed xylene" obtained from the operation of catalytic reforming contains about 20% by weight of ethylbenzene.

In addition, as the raw material of the present invention, "mixed xylene" which has been obtained by removing the larger amount of ethylbenzene as the raw material of monomeric styrene from the "mixed xylene" and contains a smaller amount of ethylbenzene may be mentioned, and another "mixed xylene" obtained from the step of producing p-xylene may be mentioned also.

"Xylene" used according to the present invention may be any one of the three isomers (i.e., o-, m- and p-xylene) or a mixture of at least two isomers of the three isomers, however, according to the kinds of the isomers, the position of the methyl groups on the benzene ring of 1,2-ditolylethane and 1-tolyl-2-phenylpropane is changed.

In conclusion, the weight ratio of ethylbenzene to xylene in the mixed raw material for use in the reaction of "coupling by side-chain dehydrogenation" to produce the diarylalkanes suitable as the solvent of chromogenic dye-precursor material for the pressure-sensitive recording paper sheet according to the present invention is 5:95 to 30:70, preferably from 8:92 to 20:80.

The diarylalkanes formed by the above-mentioned reaction comprises the following three compounds.
1,2-ditolylethane,
1-tolyl-2-phenylpropane and
2,3-diphenylbutane(dl-isomer and meso isomer).

The ratio of formation of the above-mentioned three compounds depends on the ratio of ethylbenzene to xylene in the raw material. For instance, in the case where the ratio of ethylbenzene to xylene is 1:1, the ratio of formation of 1,2-ditolylethane, 1-tolyl-2-phenylpropane and 2,3-diphenylbutane is approximately 1:2:1.

Since 2,3-diphenylbutane is a substance which easily crystallizes at low temperatures, in the case where the content of 2,3-diphenylbutane in the diarylalkanes which is to be used as the solvent is over 10% by weight, 2,3-diphenylbutane crystallizes out from the diarylalkanes at a low temperature of not higher than $-5°$ C., and such a situation is not desirable.

Accordingly, by mixing ethylbenzene and xylene at ratio of 5:95 to 30:70, preferably 8:92 to 20:80 by weight as has been shown above, the diarylalkanes is composed of not less than 80% by weight of 1-tolyl-2-phenylpropane and 1,2-ditolylethane and not more than 20% by weight of 2,3-diphenylbutane and the other by-products, and the ratio of 1-tolyl-2-phenylpropane and 1,2-ditolylethane is from 5:95 to 50:50, preferably from 10:90 to 40:60 by weight.

As peroxodisulfate according to the present invention, ammonium peroxodisulfate, alkali metal peroxodisulfate, alkaline earth peroxodisulfate and aluminum peroxodisulfate may be mentioned. From the view points of availability and solubility in water, ammonium peroxodisulfate can be used most generally. Among the other salts, there is a member which is difficultly isolated as solid, however, in the case where a solution of the salt is obtained as the result of electrolytical formation, the solution can be used in the reaction of of "coupling by side-chain dehydrogenation" according to the present invention.

In the aqueous solution of peroxodisulfate, which is used in the above-mentioned reaction, the preliminary coexistence of sulfate ions is preferable.

As has been described, peroxodisulfate becomes to peroxodisulfate ion in water, and the ion after participating the reduction of the alkylated aromatic compound changes into sulfate ion or hydrogen-sulfate ion. On the other hand, the peroxodisulfate ion can be regenerated by the electrolytic oxidation of sulfate ion, and in the regenerating reaction, it is a necessary condition to keep the concentration of sulfate ion ($SO_4{}^{2-}$) at a high degree for obtaining a high current efficiency.

Namely, as the suitable conditions for producing peroxodisulfate from an aqueous solution containing sulfate ions and/or hydrogensulfate ions by electrolytic oxidation, it has been pointed out that (1) the concentration of sulfate ions is as high as possible, (2) the temperature of electrolyte is low, (3) the current density is high and (4) an auxiliary agent such as $SCN^-$, $F^-$, $Cl^-$ and $CN^-$ is used (refer to "Theory and Application of Electrochemistry (in Japanese)" by KAMEYAMA, Naoto, Volume 2, 1953 Publ. by MARUZEN).

However, in the reaction of "coupling by side-chain dehydrogenation" of alkylated aromatic compounds, the high concentration of sulfate ion causes the reduction of the selectivity for formation of the dimerized product and such a condition is not desirable. According to the present invention, in order to satisfy the requirements which are contrary to each other, the reduction of the selectivity for the formation of the coupled product is prevented by (1) maintaining the concentration of sulfate ions at a certain high degree and (2) elevating the reaction temperature in the step of coupling.

It is preferable that the concentration of sulfate ions in the aqueous solution at the time of finishing the reaction of "coupling by side-chain dehydrogenation" is 2 to 4 mol/liter, more preferably 2.5 to 3.5 mol/liter. In the case of under 2 mol/liter, since the current efficiency for the regeneration of peroxodisulfate in the electrolytic step is remarkably reduced, such a condition is not desirable. On the other hand, in the case of over 4 mol/liter, since the reaction efficiency of the reaction of "coupling by side-chain dehydrogenation" is reduced in a considerable degree, such a condition is not desirable.

As the salt of sulfuric acid to be coexisted with peroxodisulfate, sodium sulfate, potassium sulfate, ammonium sulfate and the like may be mentioned, and ammonium sulfate is preferable from the viewpoint of solubility.

The stoichiometric ratio of the mixture of ethylbenzene and xylene to peroxodisulfate for converting the whole amount of ethylbenzene and xylene into the dimers is 2:1, however, because of the occurrence of various side reactions, the above-mentioned stoichiometric ratio does not necessary give the most favorable result.

Although the coupling is ordinarily represented by the conversion of the raw material(s) and the selectivity for forming the objective product, in the reaction according to the present invention, the amount of the dimer formed from one mol of peroxodisulfate (referred to as "utilization rate of peroxodisulfate") is important from the economical view point. Although one mol of the dimer is formed from one mol of peroxodisulfate while consuming 2 mols of the raw materials (the mixture of ethylbenzene and xylene), the utilization rate of peroxodisulfate is reduced because of the occurrence of various side reactions which consume peroxodisulfate. In addition, it has been known that peroxodisulfate decomposes in the aqueous solution thereof while generating molecular oxygen, and the utilization rate of peroxodisulfate is reduced also by such a decomposition.

The prevention of the self-decomposition of peroxodisulfate can be attained by adding peroxodisulfate into the preliminarily heated mixture of ethylbenzene and xylene. In addition, the improvement of the utilization rate of peroxodisulfate is attained by making the ratio of the mixture of ethylbenzene and xylene to peroxodisulfate larger than the above-mentioned stoichiometric ratio (2:1).

It is preferable that the molar ratio of the mixture of ethylbenzene and xylene to peroxodisulfate is not less than 2:1, preferably in the range of from 2.5:1 to 4.5:1.

In the case where the molar ratio is under 2:1, the utilization rate of peroxodisulfate is not so high, and also in the case where the molar ratio is over 4.5:1, the extent of improvement of utilization rate of peroxodisulfate is small and the unreacted raw material(s) remains in an unnecessary extent, so, the above-mentioned two cases are not desirable.

The actual mode of the reaction of "coupling by side-chain dehydrogenation" of ethylbenzene and xylene according to the present invention will be exemplified as follows.

Into an autoclave provided with a stirrer, a mixture of ethylbenzene and xylene as the raw material and an aqueous solution of ammonium peroxodisulfate are continuously supplied while maintaining the temperature in the autoclave at a temperature of not less than 100° C., preferably 120° to 200° C., more preferably 150° to 180° C. The reaction mixture is continuously drawn out so as to maintain the amount of the mixture of ethylbenzene and xylene and the aqueous solution of ammonium peroxodisulfate in the autoclave to constant. In addition, the supplying ratio of the mixture of ethylbenzene and xylene to ammonium peroxodisulfate is not less than the stoichiometric ratio, preferably 2.5:1 to 4.5:1. It is desirable to preliminarily add ammonium sulfate (or sulfuric acid according to the situation) to the aqueous solution of ammonium peroxodisulfate so that the concentration of sulfate ions in the aqueous solution at the outlet of the autoclave becomes to 2 to 4 mol/liter.

The reaction mixture drawn out from the autoclave is separated into an organic layer and an aqueous layer following the ordinary method. From the organic layer, the unreacted raw material and the objective product are separated and recovered. In addition, the thus recovered unreacted raw material is supplied to the step of the reaction of "coupling by side-chain dehydrogenation", and the aqueous layer is supplied to the step of electrolysis and ammonium peroxodisulfate is regenerated therefrom by electrolytic oxidation. The thus regenerated ammonium peroxodisulfate is, in ordinary cases, supplied to the step of the reaction of "coupling by side-chain dehydrogenation".

As has been described, a small amount of ions such as $SCN^-$, $F^-$, $Cl^-$ or $CN^{31}$ is preferably added in the step of electrolytic oxidation.

The actual mode in the case of batch-wise operation is exemplified as follows.

Into an autoclave provided with a stirrer, a mixture prepared by admixing a mixture of ethylbenzene and xylene with water, sulfuric acid or an aqueous solution of a salt of sulfuric acid is supplied, and the thus supplied mixture is heated to a temperature of not less than 100° C., preferably 120° to 200° C., more preferably 150° to 180° C. while stirring thereof.

After attaining to the predetermined temperature, an aqueous solution of ammonium peroxodisulfate is added dropwise to the thus heated and stirred mixture to carry out the reaction.

The molar ratio of the mixture of ethylbenzene and xylene to ammonium peroxodisulfate is the same as in the continuous reaction.

After the reaction is over, the reaction mixture is cooled nearly to room temperature and the reaction mixture is separated into an organic layer and an aqueous layer. Thereafter both the layers are treated as in the continuous system.

The above-mentioned processes are the exemplification of the procedures in the case of effecting the present invention, and the present invention is not limited thereby. Namely, the reaction of "coupling by side-chain dehydrogenation" may be carried out by either of the continuous- and batch processes.

In addition, the reaction of "coupling by side-chain dehydrogenation" may be carried out without effecting the regeneration of peroxodisulfate.

The diarylalkanes thus obtained by the reaction of "coupling by side-chain dehydrogenation" of ethylbenzene and xylene, which contains not less than 80% by weight of 1-tolyl-2-phenylpropanes and 1,2-ditolylethanes has the aforementioned specificities as the solvent of chromogenic dye-precursor material for the pressure-sensitive recording paper sheet, and crystals are not precipitated therefrom even at low temperatures. In addition, the pressure-sensitive recording paper sheet prepared by using the above-mentioned diarylalkanes is excellent in the stability in preservation of the colour-developed image obtained by pressure-sensitive recording for a long time while showing not less than 70% of the stability in preservation, is almost odorless and shows an excellent colour-developing activity of not less than 70% in the coldest season, for instance, at a low temperature of not higher than $-5°$ C.

According to the present invention, the diarylalkanes are formed by reacting a mixture of ethylbezene and xylene in the presence of an aqueous solution of peroxodisulfate at a temperature of not less than 100° C., thereby causing a dehydrogenation reaction at the position of the alkyl group of the alkyl-substituted aromatic compound, and even in the presence of sulfate ions at a high concentration, the by-production of aromatic compounds having oxygen-containing side-chain(s) is small enough. In addition, the utilization rate of peroxodisulfate in the above-mentioned reaction is very high.

Furthermore, since the concentration of sulfate ions in the above-mentioned reaction is high, it is able to regenerate peroxodisulfate with a sufficient current efficiency of elecrolysis from the aqueous solution drawn out from the main reaction system.

The invention will be concretely explained while referring to the non-limitative examples and the comparative examples as follows.

In addition, the conditions in gas-chromatographic analysis and high performance liquid chromatographic analysis (hereinafter referred to as HPLC analysis) are as follows.

"GAS-CHROMATOGRAPHY"

Filler of column: Dexsil 300 GC (5% Chromosorb W AW DMCS 80/100),
Column: made of glass tube of 2.6 mm in inner diameter and 2.1 m in length
Temperature of column: from 50° to 300° C. at a temperature elevating rate of 15° C./min
Carrier gas: Helium at a flow rate of 60 ml/min
Detector: FID

"HPLC"

Column: Shodex ODS pak F 411 A
Temperature: 40° C.
Eluent: an aqueous 70% solution of acetonitrile at a flow rate of 0.5 ml/min
Detector: by using ultraviolet ray of 210 nm.

EXAMPLE 1

After introducing 5 liters of a mixture of 1 liter of ethylbenzene, 1 liter of p-xylene, 2 liters of m-xylene and 1 liter of o-xylene, and 30 liters of water into a glass-lined reaction vessel of a capacity of 50 liters provided with a stirrer, the content of the reaction vessel was heated from outside by steam to maintain the content at 130° C., and then, 8 liters of an aqueous solution of 4.5 kg of ammonium peroxodisulfate were added to the mixture within 1.5 hours.

After cooling the reaction mixture, the organic layer was separated therefrom and analyzed by gas-chromatography. The results are shown in Table 1 as follows.

TABLE 1

| Component | Composition (% by weight) |
|---|---|
| 1,2-ditolylethane(s) | 46.4 |
| 1-tolyl-2-phenylpropane(s) | 9.3 |
| 2,3-diphenylbutane(s) | 0.8 |
| tolualdehyde and acetophenone | 2.8 |
| unreacted raw material(s) | 36.3 |
| others | 4.4 |

Accordingly, the conversion rate of the raw materials was 63.7%, the selectivity for formation of the dimer was 88.7% and the utilization rate of peroxodisulfate in the formation of the dimer was 58.7%.

EXAMPLE 2

Into a glass autoclave provided with a stirrer (made by TAIATSU Glass Industry Co., Ltd., Type TEM-V, Capacity of one liter), 50 ml of a mixture of 10 mol % of ethylbenzene and 90 mol % of m-xylene and 550 ml of an aqueous solution of ammonium peroxodisulfate of the following composition were preliminarily introduced, and the thus introduced substances were heated to 140° C. by a transparent heating body installed on the outer surface of the autoclave while stirring the content of the autoclave.

Composition of the Aqueous Solution of Ammonium Peroxodisulfate

Ammonium peroxodisulfate: 0.25 mol/liter
Ammonium sulfate: 2.35 mol/liter
Sulfuric acid: 0.15 mol/liter Thereafter, the mixture of ethylbenzene and xylene of the same composition as above and the aqueous solution of ammonium peroxodisulfate of the above-mentioned composition were supplied into the autoclave continuously from the nozzles provided therewith at the rates of 0.426 mol/hour and 580 ml/hour respectively. In order to maintain the inner temperature of the autoclave at 140° C. and to maintain the amount of the liquid mixture in the autoclave at 600 ml, the reaction mixture was continously drawn out from the autoclave via another nozzle.

From the thus drawn reaction mixture at the time of 4 hours from the beginning of the reaction, the organic layer was separated and the composition thereof was analized by gas-chromatography and HPLC, the results being shown in Table 2.

TABLE 2

| Component | Composition (% by weight) |
|---|---|
| 1,2-ditolylethane(s) | 40.3 |
| 1-tolyl-2-phenylethane(s) | 3.8 |
| 2,3-diphenylbutane(s) | 0.1 |
| tolualdehyde and acetophenone | 0.9 |
| unreacted raw material | 46.3 |
| others | 8.6 |

Accordingly, the conversion rate of the raw materials was 53.7%, the selectivity for formation of the dimer was 82.3% and the utilization rate of peroxodisulfate in the formation of the dimer was 69.0%.

EXAMPLE 3

In the same manner as in Example 2 except for the composition of the mixture of ethylbenzene and xylenes shown in Table 3, the amount of supply of the aqueous solution of ammonium peroxodisulfate of 600 ml/hour and the reaction temperature of 150° C., the reaction of "coupling by side-chain dehydrogenation" was carried out.

TABLE 3

Composition of the mixture or ethylbenzene and xylene shown by the amount of supply of the component per hour

| Component | Supplying rate |
|---|---|
| ethylbenzene | 0.12 mol/hour |
| p-xylene | 0.12 mol/hour |
| m-xylene | 0.239 mol/hour and |
| o-xylene | 0.12 mol/hour |

The composition of the thus drawn reaction mixture after 4 hours of the beginning of the reaction is shown in Table 4.

TABLE 4

| Component | Composition (% by weight) |
|---|---|
| 1,2-ditolylethane(s) | 24.9 |
| 1-tolyl-2-phenylpropane(s) | 5.5 |
| 2,3-diphenylbutane(s) | 0.2 |
| tolualdehyde and acetophenone | 1.4 |
| unreacted raw material(s) | 64.9 |
| others | 3.1 |

Accordingly, the conversion rate of the raw materials was 35.1%, the selectivity for formation of the dimer was 87.2% and the utilization rate of peroxodisulfate in the formation of the dimer was 62.1%.

EXAMPLE 4

In the same manner as in Example 2 except for the composition of ethylbenzene and xylene shown in Table 5, the supplying rate of the aqueous solution of ammonium peroxodisulfate of 600 ml/hour and the reaction temperature of 150° C., the reaction was carried out.

TABLE 5

Composition of the mixture of ethylbenzene and xylene

| Component | Rate of supply of the component |
|---|---|
| ethylbenzene | 0.178 mol/hour |
| p-xylene | 0.104 mol/hour |
| m-xylene | 0.208 mol/hour |

TABLE 5-continued

Composition of the mixture of ethylbenzene and xylene

| Component | Rate of supply of the component |
|---|---|
| o-xylene | 0.104 mol/hour |

The composition of the organic matter drawn out after 4 hours of the beginning of the reaction is shown in Table 6.

TABLE 6

| Component | Composition (% by weight) |
|---|---|
| 1,2-ditolylethane(s) | 17.9 |
| 1-tolyl-2-phenylpropane(s) | 6.7 |
| 2,3-diphenylbutane(s) | 0.5 |
| tolualdehyde and acetophenone | 1.7 |
| unreacted raw materials | 66.0 |
| others | 7.2 |

Accordingly, the conversion rate of the raw materials was 34.0%, the selectivity for formation of the dimer was 73.8% and the utilization rate of peroxodisulfate in the formation of the dimer was 50.0%.

COMPARATIVE EXAMPLE 1

Into a 500 ml-four necked flask provided with a stirrer, 21.2 g of ethylbenzene, 22.8 g of ammonium peroxodisulfate and 400 ml of water were introduced, and the thus introduced materials were reacted at a temperature of 89° to 93° C. for one hour.

The composition of the organic layer of the reaction product was as follows.
2,3-diphenylbutane: 6.0 mol %
acetophenone: 16.3 mol %
unreacted ethylbenzene: 75.0 mol %

Accordingly, the conversion rate of ethylbenzene was 25%, the selectivity for formation of the dimer was 24% and the utilization rate of peroxodisulfate in the formation of the dimer was 6%. In addition, acetophenone was the major product.

COMPARATIVE EXAMPLE 2

In the same manner as in Comparative Example 1 except for p-xylene instead of ethylbenzene in Comparative Example 1, the reaction was carried out. The results were shown as follows.
1,2-ditolylethane(s): 23.5 mol %
p-tolualdehyde: 4.1 mol %
unreacted p-xylene: 68.8 mol %
others: 3.6 mol %

Accordingly, the conversion rate of p-xylene was 31.2%, the selectivity for formation of the dimer was 75% and the utilization rate of peroxodisulfate in the coupling was 23.5%.

As are clearly seen in Comparative Examples, in the reaction at low temperatures, the formation of the aromatic compounds having the oxygen-containing side-chain(s) predominated, and the utilization rate of peroxodisulfate in coupling was remarkably low.

EXAMPLE 5

Synthesis of a Solvent

Into a glass-lined reaction vessel of a capacity of 50 liters, a mixed raw material of 6% by weight of ethylbenzene and 94% by weight of xylenes (23.5% by weight of p-xylene, 47.0% by weight of m-xylene and 23.5% by weight of o-xylene) was continuously supplied at a rate of 3.6 liters/hour, and in the same time, an aqueous solution of 0.25 mol/liter of ammonium peroxodisulfate, 2.35 mol/liter of ammonium sulfate and 0.15 mol/liter of sulfuric acid was also supplied continuously at a rate of 30 liters/hour.

Thereafter, the content of the reaction vessel was reacted at 150° C. while drawing the reaction mixture out from the reaction vessel, thereby keeping the amount of the liquid in the reaction vessel at 30 liters.

The reaction product was subjected to separation by distillation, thereby obtaining 800 ml of the dimer fraction of the composition shown in Table 7 as follows.

TABLE 7

| Component | Composition (% by weight) |
| --- | --- |
| 1,2-ditolylethane(s) | 92.4 |
| 1-tolyl-2-phenylpropane(s) | 7.1 |
| 2,3-diphenylbutane(s) | 0.5 |

The kinematic viscosity of the mixed solvent was 4.3 cst at 40° C. and the specific gravity thereof was 0.975 at 15° C.

Preparation of Microcapsules

A solution obtained by dissolving 3.4 g of crystalviolet-lactone and 1.1 g of a red dyestuff (made by SHIN-NISSO-KAKO Co., Ltd. under the mark of PSD-V) in 150 g of the solvent obtained as above was added to a solution prepared from 30 g of gelatine and 270 g of water, and the thus obtained mixture was emulsified. After adding a solution prepared by dissolving 30 g of gum arabic in 270 g of water to the emulsion, the thus obtained mixture was stirred while keeping thereof at 50° C., and 1000 ml of water were added to the mixture. Then the pH of the mixture was reduced slowly to 4.4 by using an aqueous 50% solution of acetic acid, thereby causing coacervation. After cooling the thus formed coacervate to 10° C. to harden the membrane of the thus formed microcapsules, 20 ml of an aqueous 25% solution of glutaraldehyde were added to the coacervate. Then, the pH of the coacervate was adjusted to 9 by using an aqueous 10% solution of sodium hydroxide, thereby hardening the membrane of the microcapsule to complete the microencapsulation.

Preparation of a Pressure Sensitive Recording Paper Sheet

By coating the thus obtained microcapsules on one side of a weighed sheet of paper of 45 g/m² in a dried amount of 5 g/m², a sheet of CB paper was obtained, and by combining the thus prepared sheet of CB paper with a sheet of CF paper prepared by an ordinary process, a pressure-sensitive recording paper sheet was obtained.

EXAMPLE 6

A solvent was prepared in the same manner as in Example 5 except for a mixed raw material of 15% by weight of ethylbenzene and 85% by weight of "mixed xylene" of 21.2% by weight of p-xylene, 42.5% by weight of m-xylene and 21.3% by weight of o-xylene. The composition of the thus obtained mixed solvent is shown in Table 8 as follows.

TABLE 8

| Component | Composition (% by weight) |
| --- | --- |
| 1,2-ditolylethane(s) | 82.3 |
| 1-tolyl-2-phenylpropane(s) | 16.7 |
| 2,3-diphenylbutane(s) | 1.0 |

The kinematic viscosity of the thus obtained solvent was 4.4 cst at 40° C. and the specific gravity thereof was 0.976 at 15° C.

A pressure-sensitive recording paper sheet was prepared by using the thus obtained solvent following the method of preparing the microcapsule and the method of preparing a pressure-sensitive recording paper sheet shown in Example 5.

EXAMPLE 7

A mixed solvent was prepared in the same manner as in Example 5 except for a raw material of 20% by weight of ethylbenzene and 80% by weight of "mixed xylene" of 20.0% by weight of p-xylene, 40.0% by weight of m-xylene and 20% by weight of o-xylene. The composition of the thus obtained mixed solvent is shown in Table 9.

TABLE 9

| Component | Composition (% by weight) |
| --- | --- |
| 1,2-ditolylethane(s) | 75.7 |
| 1-tolyl-2-phenylpropane(s) | 23.1 |
| 2,3-diphenylbutane(s) | 1.2 |

The kinematic viscosity of the thus obtained solvent was 4.4 cst at 40° C. and the specific gravity thereof was 0.976 cst at 15° C.

Thereafter, a pressure-sensitive recording paper sheet was prepared by using the thus prepared solvent while following the method of preparing the microcapsules and the method for preparing the pressure-sensitive recording paper sheet shown in Example 5.

COMPARATIVE EXAMPLE 3

Into a one-liter round bottom flask provided with a cooler and a stirrer, 500 g of toluene and 30 g of aluminum chloride were introduced, and 40 g of 1,1-dichloroethane were dropped into the flask while stirring the content of the flask at 60° C., thereby carrying out the reaction.

After the reaction was over, the reaction mixture was cooled to 20° C., aluminum chloride was removed therefrom and the remaining material was washed with water. The thus obtained reaction product was subjected to distillation to obtain 50 g of 1,1-ditolylethane.

Thereafter, a pressure-sensitive recording paper sheet was prepared by using the thus obtained 1,1-ditolylethane while following the method of preparing the microcapsules and the method for preparing the pressure-sensitive recording paper sheet shown in Example 5.

COMPARATIVE EXAMPLE 4

A pressure-sensitive recording paper sheet was prepared while using each one of diisopropylnaphthalene, 1-xylyl-1-phenylethane, xylylphenylmethane, butylbiphenyl and partially hydrogenated terphenyl which have been put into practical use at present as the solvent for chromogenic dye-precursor material and following the method of preparing microcapsules and the method for preparing the pressure-sensitive recording paper sheet shown in Example 5.

TEST EXAMPLE 1

The present experiment is the test of the stability in preservation in the colour-developed image of the pressure-sensitive recording paper sheet.

Namely, each one of the pressure-sensitive recording paper sheet prepared respectively in Examples 5 to 7 and Comparative Examples 3 to 4 was superposed with CCP resin CF (Carbonless Copying Paper resin CF, made by JUJO SEISHI Co., Ltd.), and a colour was made to develope by typewriting on the thus superposed material (the sheet and the resin) while using a typewriter (made by Olivetti Co.).

After keeping the thus colour-developed pressure-sensitive recording paper sheet in a dark place for 24 hours to complete the colour-development, the colour density of the sheet was determined by a tester of reflexed colour density (made by MACBETH Co.), and the thus obtained value of the colour density was used as a standard.

After exposing a colour-developed pressure-sensitive recording paper sheet prepared by the same methods as above to lights for 10 hours in a weather meter (made by TOYO RIKAGAKU Co., Ltd., under the registered trade name of STANDARD SUNSHINE WEATHER METER, type: WE-SUN-HC) without spraying water, the colour density thereof was determined as above.

The stability in preservation in the colour-developed image of the thus prepared pressure-sensitive recording paper sheet (referred to as "Stability") was obtained by the following formula:

$$\text{Stability} = \frac{\text{Colour density after exposing}}{\text{Standard colour density}} \times 100$$

The results of the test are shown in Table 10.

TEST EXAMPLE 2

The present experiment is the odor test of the solvent of chromogenic dye-precursor material for a pressure-sensitive recording paper sheet.

Namely, each one of the solvents prepared in Examples 3 to 7 and Comparative Example 3, and the solvent shown in Comparative Example 4 was subjected to panel test concerning the odor by 20 persons selected unintentionally. The test results are also shown in Table 10.

In this connection, the test results are shown by the following remarks.

| Remark | Result |
| --- | --- |
| A | Odorless |
| B | Almost odorless |
| C | Odoriferous |
| D | Unpleasantly odoriferous |

TEST EXAMPLE 3

The present experiment is the colour-developing rate under the cold environment of the pressure-sensitive recording paper sheet.

After subjecting each one of the pressure-sensitive recording paper sheet prepared in Examples 5 to 7 and Comparative Examples 3 to 4 to a calender roll at ordinary temperature, thereby developing a colour, the colour density on the thus colour-developed pressure-sensitive recording paper sheet was determined by the tester of reflexed colour density(refer to Test Example 1). The thus obtained value of colour density was adopted as the standard.

On the other hand, each of the same pressure-sensitive recording paper sheet was made to develop colour by the same manner as above in a temperature constant room at $-5°$ C., and the colour density of the thus colour-developed sheet was determined.

The colour-developing rate is represented by the percentage of the thus obtained colour density to standard value.

The results are also shown in Table 10.

TEST EXAMPLE 4

The present experiment is the test on the precipitate of crystals from the solvent of chromogenic dye-precursor material for the pressure-sensitive recording paper sheet.

Namely, each one of the solvents obtained in Examples 5 to 7 and Comparative Example 3 and the solvents shown in Comparative Example 4 was introduced into a 50 ml-glass bottle, and after introducing a piece of aluminum foil thereinto as a sharp-edge, the flask was kept for 30 days in a thermostat at $-30°$ C.

During the 30 days, the state of precipitation of crystals in the flask was observed every 10 days and the results are shown in the following type of evaluation.

| Remark | Result |
| --- | --- |
| A | Precipitation of crystals not observed |
| B | Precipitation of crystals observed on the 20th day |
| C | Precipitation of crystals observed on the 10th day. |

As the solvent of chromogenic dye-precursor material for the pressure-sensitive recording paper sheet, which is excellent in the stability in preservation of the colour-developed image and in the colour-developing activity at low temperatures and is almost odorless in addition to the specificities of the conventional solvent of chromogenic dye-precursor material for the pressure-sensitive recording paper sheet, those showing the following data of evaluation as the results of the tests such as (1) the stability in preservation of the colour-developed image, (2) odor, (3) the activity of colour-development at low temperatures and (4) the precipitation of crystals therefrom at low temperatures are the solvent of chromogenic dye-precursor material for the pressure-sensitive recording paper sheet, which could be used for practical use.

DATA (1) Stability (refer to Test Example 1): higher than 70%,
(2) Odor: higher than B,
(3) Colour-developing activity at low temperatures: higher than 70%, and
(4) Precipitation of crystals at low temperatures: A As are clearly seen in Table 10, only the solvents according to the present invention satisfied the above-mentioned conditions.

TABLE 10

| Example or Comparative Example | Name of compound | Stability (%) | Odor | Activity in colour-developing | Precipitation of crystals |
|---|---|---|---|---|---|
| Example 5 | Mixture of 1-tolyl-2-phenyl-propane and 1,2-ditolylethane | 80 | B | 75 | A |
| Example 6 | Mixture of 1-tolyl-2-phenyl-propane and 1,2-ditolylethane | 76 | B | 73 | A |
| Example 7 | Mixture of 1-tolyl-2-phenyl-propane and 1,2-ditolylethane | 71 | B | 71 | A |
| Comparative Example 3 | 1,1-ditolylethane | 70 | C | 72 | — |
| Comparative Example 4 | diisopropylnaphthalene | 72 | B | 32 | C |
| | 1-xylyl-1-phenylethane | 72 | D | 48 | — |
| | xylylphenylmethane | 93 | D | 75 | — |
| | butylbiphenyl | 70 | D | 51 | — |
| | partially hydrogenated terphenyl | 90 | B | less than 20 | — |

What is claimed is:

1. A pressure-sensitive recording paper sheet comprising a paper sheet having a layer of microcapsules containing a chromogenic dye-precursor and a solvent for said dye-precursor, wherein said solvent comprises diarylalkanes which contain not less than 80% by weight of a mixture of 1-tolyl-2-phenylpropane and 1,2-ditolylethane, and are obtained by subjecting ethylbenzene and xylene to "coupling by side-chain dehydrogenation".

2. The pressure-sensitive recording paper sheet according to claim 1, wherein the weight ratio of 1-tolyl-2-phenylpropane to 1,2-ditolylethane of said solvent is 5:95 to 50:50.

UNITED STATES PATENT AND TRADEMARK OFFICE
CERTIFICATE OF CORRECTION

PATENT NO. : 4,786,630

DATED : November 22, 1988

INVENTOR(S) : Nakamura, et al.

It is certified that error appears in the above-identified patent and that said Letters Patent is hereby corrected as shown below:

On the Title Page, Item [73], correct the spelling of the assignee's name from "Kaishi" to --Kaisha--.

Signed and Sealed this

Eleventh Day of July, 1989

Attest:

DONALD J. QUIGG

Attesting Officer

Commissioner of Patents and Trademarks